United States Patent [19]

Jöbsis et al.

[11] Patent Number: 4,510,938

[45] Date of Patent: Apr. 16, 1985

[54] BODY-MOUNTED LIGHT SOURCE-DETECTOR APPARATUS

[75] Inventors: Frans F. Jöbsis; Hans H. Keizer; Ronald F. Overaker, all of Durham, N.C.

[73] Assignee: Duke University, Inc., Durham, N.C.

[21] Appl. No.: 460,578

[22] Filed: Jan. 24, 1983

Related U.S. Application Data

[63] Continuation-in-part of Ser. No. 289,413, Aug. 3, 1981, Pat. No. 4,380,240.

[51] Int. Cl.³ .............................................. A61B 5/00
[52] U.S. Cl. .................................................. 128/633
[58] Field of Search ............... 128/633, 640, 664, 665, 128/666, 667, 673, 687

[56] References Cited

U.S. PATENT DOCUMENTS

| 3,170,459 | 2/1965 | Phipps et al. | 128/640 |
| 3,602,213 | 8/1971 | Howell et al. | 128/666 |
| 4,223,680 | 9/1980 | Jöbsis | 128/633 |

Primary Examiner—William E. Kamm
Attorney, Agent, or Firm—B. B. Olive

[57] ABSTRACT

Means are provided for securing to the human body a light source housing and a light detector housing used for monitoring metabolism, said means comprising sockets adapted to fit over the housings and having tab members adapted to be adhesively secured to the body to maintain the respective light source and light detector housings in spaced relation on the body and further comprising a light-shielded pad fitted over said sockets and adhered to the body to provide light shielding for the light source and light detector confined in said housings.

2 Claims, 17 Drawing Figures

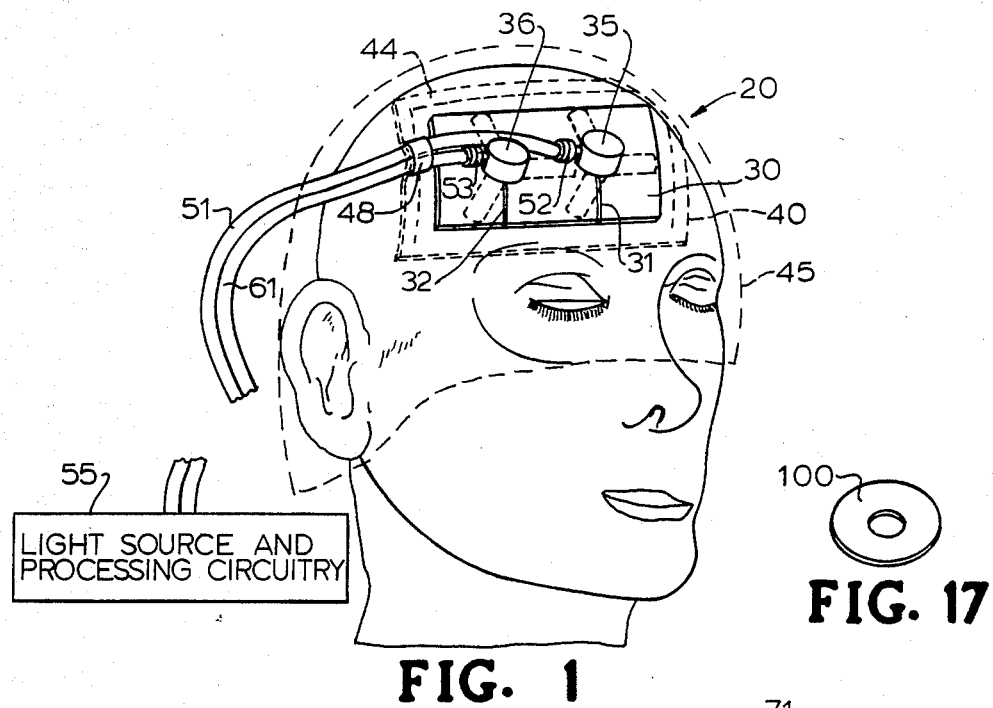
FIG. 1
FIG. 17
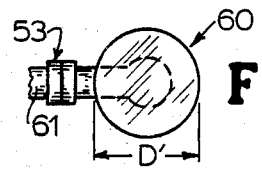
FIG. 2
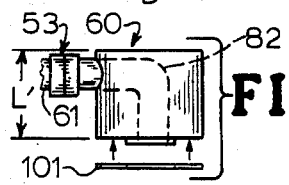
FIG. 3
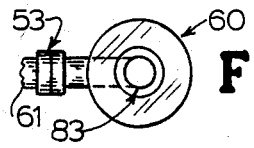
FIG. 4
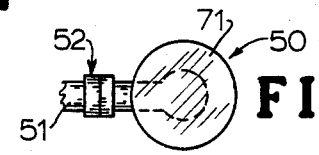
FIG. 5
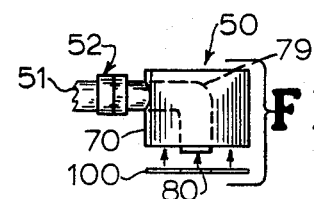
FIG. 6
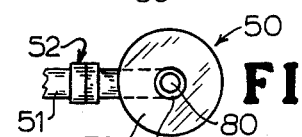
FIG. 7
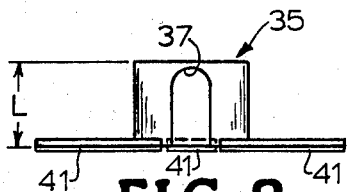
FIG. 8
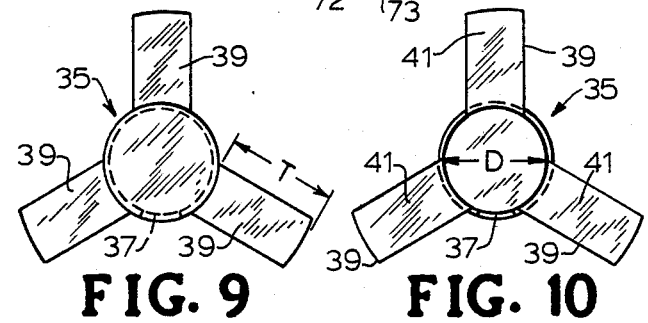
FIG. 9    FIG. 10

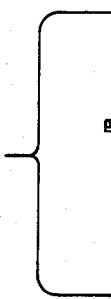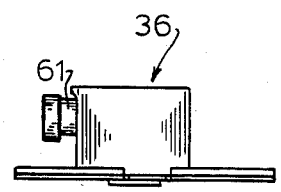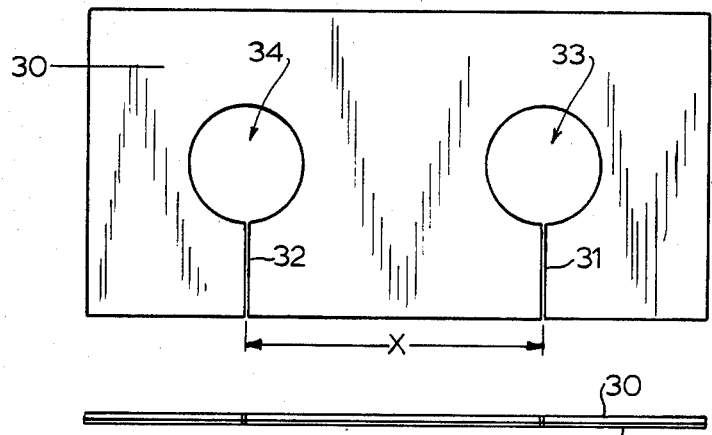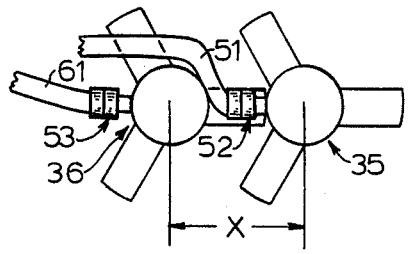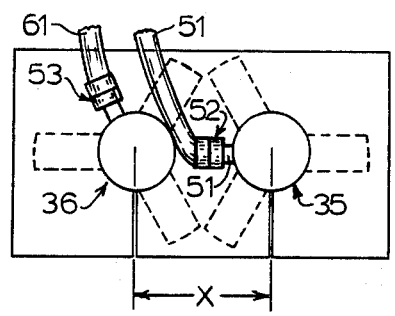

BODY-MOUNTED LIGHT SOURCE-DETECTOR APPARATUS

DESCRIPTION

The invention described herein was made in the course of work under a grant or award from the Department of Health, Education and Welfare.

CROSS-REFERENCE TO RELATED APPLICATIONS AND PATENTS

This application relates to and constitutes an improvement on the subject matter of U.S. Pat. Nos. 4,223,680, entitled "Method and Apparatus for Monitoring Metabolism in Body Organs In Vivo"; 4,281,645, entitled "Method and Apparatus for Monitoring Metabolism in Body Organs"; and 4,321,930, entitled "Apparatus for Monitoring Metabolism in Body Organs". This application further constitutes a continuation-in-part of the subject matter of copending application Ser. No. 289,413, filed Aug. 3, 1981 and now Pat. No. 4,380,240, entitled "Improved Apparatus for Monitoring Metabolism in Body Organs".

TECHNICAL FIELD

The invention relates to spectrophotometric apparatus for monitoring selected characteristics of the human body in vivo and more specifically to apparatus for mounting associated light source and light detector apparatus on the body, particularly on the head of a human patient.

BACKGROUND ART

In the prior related patents and copending application referred to above there has been described a spectrophotometric method and apparatus directed to non-invasive, continuous, atraumatic, in vivo, in situ monitoring of metabolism in a body organ. In the described method and apparatus, measuring and reference wavelengths within the near-infrared region, i.e., 700–1300 nm, are utilized with light source and light detector devices mounted on the body for non-invasive, continuous, atraumatic, in vivo, in situ monitoring of oxidative metabolism by monitoring oxygen sufficiency in an internal organ, e.g., the brain, of a human or animal body. Advantage is taken of the critical characteristic of cellular enzyme cytochrome a, $a_3$ (also known as cytochrome c oxidase and identified by EC 1.9.3.1) within the optical path and within the radiated portion of the selected organ for absorbing the selected measuring wavelength and for light of this measuring wavelength, as well as at least one reference wavelength within the same defined infrared region and at a low, non-hazardous level of intensity to be detectable at the end of a relatively long transillumination or reflectance path, e.g., of several centimeters length, which may include substantial content of bone as well as soft tissue and skin. Variations in metabolic and circulatory parameters during measuring are recognized and the selection of wavelengths, circuitry and method also provide techniques for compensating for changes in blood volume in the organ being monitored, for continuous monitoring of hemoglobin oxygenation and blood volume, for intermittent monitoring of blood flow rate, for skin blood flow effects and variations in the light source, e.g., laser diode, output.

A useful background of the prior art may be had by making reference to the discussion of the prior art in the mentioned related prior patents and to the light source and light detecting structures described in U.S. Pat. Nos. 3,527,932; 3,674,008; 3,638,640; 3,704,706; and 4,077,399.

In the context of the mentioned related prior patents and copending application and related prior art, the present invention is primarily concerned with the means for mounting the light source-light detecting devices on the body, particularly on the head for brain monitoring. Thus, the present invention is primarily intended to provide an improvement over the light source-light detecting structure shown in the prior patents and in copending application Ser. No. 289,413 as well as over all known prior art deemed relevant to the invention.

Taking all of the foregoing into account, further development and experimentation with the spectrophotometric apparatus and method of the prior related patents and particularly with the strap structure for mounting the light source-light detecting devices on the body as set forth in copending application Ser. No. 289,413, has revealed a need for an even further improved means for securing, spacing and shielding the light source as well as the light detector when mounted on the body and such that a strap is not required. This needed improvement is of particular significance in those medical and surgical procedures in which the patient is prone and the head of the patient is required to be tilted back, either for examining or introducing substances or instruments into the throat of the patient. In addition to providing a light source-detector mounting arrangement which does not require use of a strap for attachment and securement, there is a continuing need for the mounting structure in whatever form it is made to be reproducible in a low cost form and where necessary in a form lending itself to a single end use application for at least the most inexpensive components of the mounting structure so as to minimize sterilizing procedures for those components of the mounting structure not suited to a single end use.

The achievement of these various needed and other improvements thus becomes the object of the invention and other objects will be revealed as the description proceeds.

DISCLOSURE OF INVENTION

The invention is directed to improvements in means for orienting in reference to the body, supporting on and releasably securing to the body, shielding from ambient light at the point of attachment and accurately spacing the light source and the light detector associated with remotely located spectrophotometric apparatus utilized for monitoring body functions in vivo, non-invasively and atraumatically according to the teachings of the related prior patents previously referred to.

Decisive information is provided on the parameter of oxygen sufficiency in the tissue or organ in question, in vivo. The invention apparatus, in conjunction with the apparatus and techniques of the related prior patents also provides the capability of monitoring the oxygenation state of the blood being supplied, blood volume and blood flow rate in the portion of the body being monitored and in a manner which is non-invasive and atraumatic.

The body-mounted invention apparatus is utilized in association with the near-infrared sources, timing, detecting and processing circuitry as well as the measuring techniques described in the related prior patents.

Thus, by reference to the related prior patents, it will be understood that the light source-detector mounting apparatus of the invention facilitates the carrying out of a continuous, non-invasive, in vivo, in situ monitoring of the redox state of cytochrome a, $a_3$ in the body portion of interest by using the deep, diffuse, multiple-scattered light, reflectance technique and near-infrared radiation within the range of about 700–1300 nm as referred to in the related prior patents and copending application. When the invention apparatus is applied to the head, for example, the light source and light detector components are spaced apart on the same side of the head and the light reflected and scattered back to the light source location is detected and used in the associated processing circuitry of the prior patents as a correction for skin blood volume changes. The light source-detector mounting arrangement of the invention also offers further improvements in minimizing light loss and also in minimizing the establishment of localized pressure conditions and thereby avoiding erroneous signal conditions. Of special significance is the fact that the light source-detector mounting assembly of the invention eliminates the need for a strap when the invention assembly is being used on the head of a human patient in a prone position and thus provides a substantially improved means for using the techniques of the prior related patents in those medical and surgical procedures where the head is required to be tilted back during the procedure.

With more specific reference to the actual structure employed in the improved light source-light detector body mounted apparatus of the invention, there is provided for each light source and light detector module a socket device adapted to receive the module and by means of radially extending flexible tabs to be adhesively secured to the body at the place of attachment using double-sided adhesive tape. The length of the socket tabs allows the pair of sockets holding the respective light source-light detector modules to be accurately spaced apart as required for practicing the optical monitoring techniques of the prior patents. The improved mounting apparatus of the invention also provides for a flexible light shielding pad to be adhesively secured to the body so as to cover the socket tabs and allow the remaining portions of the sockets to protrude outwardly from the pad and the appropriate interconnected optical cables to lead from the pad to the light source and processing circuitry of the related prior patents. Once the optical modules and their respective sockets have been appropriately mounted and have been suitably covered by the mentioned light shielding pad, an additional somewhat larger second light shielding pad is placed over the first pad so as to cover both the first light shielding pad, the sockets and those portions of the optical cables leading from the respective optical modules in the sockets. The second light shielding pad is adhesively secured to the body at the pad's peripheral edges employing double-sided adhesive tape. As a final light shielding procedure, a flexible light impervious cape such as previously disclosed in copending application Ser. No. 289,413 is placed over that portion of the patient's body on which the mentioned optical modules, sockets and light shielding pads have been mounted so as to further shield both the light source and modules from ambient light.

DESCRIPTION OF THE DRAWINGS

FIG. 1 is a pictorial view of the body mountable light source-light detector apparatus of the invention illustrated as being mounted on the forehead of a patient for monitoring the brain.

FIG. 2 is a top plan view of the light detector optical module.

FIG. 3 is a side view of the light detector optical module shown in FIG. 2 and showing an annular light shielding pad used in conjunction with such module.

FIG. 4 is a bottom view of the light detector optical module shown in FIG. 2.

FIG. 5 is a top plan view of the light source optical module.

FIG. 6 is a side view of the light source optical module shown in FIG. 5 and showing an annular light shielding pad used in conjunction with such module.

FIG. 7 is a bottom view of the light source module shown in FIG. 5.

FIG. 8 is a side view of a module mounting socket of the type used in the invention for receiving either a light source or light detector module and releasably securing the same to the body in spaced relation.

FIG. 9 is a top view of the module socket shown in FIG. 8.

FIG. 10 is a bottom view of the module socket shown in FIG. 8.

FIG. 11 is an exploded side view illustrating how the light detector module of FIG. 3 is assembled in the module socket of FIG. 8.

FIG. 12 is a side view of the light detector module of FIG. 8 fully nested in the module socket.

FIG. 13 is a plan view of a light shielding pad adapted to receive and shield both the light detector module and the light source module after being nested in their respective sockets with the socket tabs adhesively secured to the body in spaced relation.

FIG. 14 is an elevation view of the pad shown in FIG. 13.

FIG. 15 is a plan view in reduced size of the light detector and light source modules assembled in their respective sockets and illustrating how the socket tabs may be used as a means for accurately spacing the optical modules apart.

FIG. 16 is a plan view in reduced size of the light detector and light source modules assembled in their respective sockets and illustrating how the optical module spacing may be determined by the pad construction.

FIG. 17 is a perspective view of the annular adhesively secured light shielding pad shown in FIGS. 3 and 6.

BEST MODE FOR CARRYING OUT THE INVENTION

With the background description provided by the related prior patents, it becomes evident that when the deep reflectance technique is followed, as referred to in prior related Pat. No. 4,321,930, the means employed for introducing and implementing deep penetration of the near-infrared measuring and reference wavelengths at the point of light entry on the body, the means employed for collecting the directly and deeply reflected light at the point of light entry and the means for collecting the deeply penetrating light after being scattered and reflected from the organ, e.g., the brain, are of continuing, crucial and significant importance to obtaining meaningful measurements of the parameters desired.

It is desirable, for example, that the light source-light detector assembly secured to the body be in a form adaptable to various body shapes such as associated with the head, a limb, or torso of a human or animal subject under observation. It has also been found critically important that light shielding associated with the body-mounted light source-detector assembly be effective both as to extraneous near-infrared as well as extraneous ambient light such that the light entering the body as well as the light detected will be only those wavelengths and only from those light sources intended to be associated with the measurements. Extraneous photon energy at the measuring location which might otherwise enter the body and affect the measurements is therefore desirably absorbed by means associated with the light source-detector assembly of the invention.

It has also become increasingly evident particularly for purposes of the present invention that the light source-detector assembly secured to the body must be in a form which avoids restricting local bloodflow or any other tissue function in the area of observation so as to avoid erroneous signals. Additionally, it has been found desirable that the light source-detector elements have an improved body mounting arrangememt that not only lends itself to shielding of extraneous light but also protects the elements as the mounting assembly changes to conform to the body shape at the area of observation. Another critical feature in the light source-detector element mounting structure is that the distance between the light source and detector element centers when mounted remain substantially fixed during the measuring period and not be subject to alterations by physical changes in body geometry brought about by breathing, flexing of the body, trauma and the like. The criticality of this distance, designated X in FIGS. 14-16, has been fully discussed in the prior related patents. Another consideration is that the light source-detector assembly which is mounted on the body be in a form adapted to be fitted with quick connect-disconnect optical couplings when the application requires that the assembly be quickly coupled to and uncoupled from the timing, light source, detecting and processing circuitry typically located at least several feet away from the patient.

As another important consideration, it has been found highly desirable that the light source-detector assembly which mounts on the body be in a form lending itself to economical manufacture and so as to incorporate to the maximum extent relatively inexpensive components which, when necessary, can each be used as a single end use, disposable component. Considering the difficulty and cost of washing and sterilization, the possibility of transmitting diseases and the likelihood of contamination in surgical and accident cases in particular, the advantage of having at least some of the less expensive components of the assembly available in a prepackaged, sterilized, single end use package will be readily appreciated.

While various of the foregoing considerations have been previously taken into account in the light source-detector strap mounting assembly described in copending application Ser. No. 289,413, a need for a more versatile mounting assembly adapted for brain monitoring has arisen. In some surgical procedures in which it is desirable to monitor oxygen sufficiency in the brain, the procedure requires that the patient's head be tilted backward for admitting various instruments or substances in the throat or such backward head tilting may simply be desired surgical or medical procedure. In other medical or surgical procedures where oxygen sufficiency in the brain is desirably monitored, the patient's head may not require tilting. Particularly when it is necessary that the patient's head be tilted backward, it has been found that the releaseable strap arrangement described in copending application Ser. No. 289,413 has certain disadvantages and caution is required to see that the light source-detector assembly is not dislodged or mispositioned when the patient's head is tilted backward. However, at other times when the patient's head is not tilted backward, the strap securing arrangement of copending application Ser. No. 289,413 has proven satisfactory. Thus, in the structure of the present invention an improved light source-detector body mounting assembly has been provided in which all of the desired characteristics previously achieved and referred to have been retained while at the same time providing an improved mounting assembly especially adapted for use on the head during monitoring of the brain and which adapts to the patient's head being either tilted backward or not as required by the medical or surgical procedure involved.

With the foregoing background information and desired characteristics and objectives in mind, the description next makes reference to the drawings to illustrate how the same are achieved in the improved body mounted light source-light detector assembly of the invention and in reference to monitoring the brain for which the invention apparatus is especially advantageous.

With reference to the drawings, the improved light source-detector assembly 20 of the invention basically comprises a flexible, light shielding adhesively secured base support pad 30, a pair of module sockets 35, 36, a light source module 50, a light detector module 60, an auxiliary light shielding pad 40 and finally an overall light shielding drape 45.

Base support pad 30 is preferably formed of a tightly constructed non-elastic, black coated fabric such as found, for example, in black coated Naugahyde fabric used for automobile seats, upholstery and the like and should preferably provide sufficient flexibility to conform to the shape of the head or other part of the body of the human or animal subject being monitored. Additionally, all surfaces of pad 30 should preferably be black in color to assist in absorbing the extraneous photon energy proximate to the observation area. Positive securement of pad 30 to the body surface is facilitated by employment of a suitable pressure sensitive adhesive 38 over the entire surface of pad 30 which is adhered to the body. A removable cover sheet over adhesive 38 is desirable.

The module sockets 35, 36 are preferably formed of a molded plastic material which is both resilient and deformable to a degree suited to the invention as described. Each module socket 35, 36 provides a hollow, resilient wall housing molded with an open base end and closed upper end and so as to snugly receive a respective light source module 50 or light detector module 60. In a preferred form, the inner diameter D and inner length L of sockets 35, 36 are of standard size as are the outer diameter D' and outer length L' of modules 50, 60. As best illustrated in FIGS. 1, 8, and 12, each module socket 35, 36 will also be noted as having an open slot 37 for receiving the respective optical cables 51, 61 leading from the respective optical modules 50, 60. Each respective socket 35, 36 is thus assembled with a respective optical module 50 or 60 as illustrated by way of example in FIGS. 11 and 12 with respect to the assembly of the socket 36 with the light detector module 60.

Optical cables 51, 61 made up of bundles of optical fibers may lead directly to the light source and processing circuitry 55 of the prior related patents with no intervening optical coupling and thereby minimize light loss. Alternatively, it is sometimes desirable that means be provided enabling the invention assembly 20 to be quickly optically coupled and uncoupled at the body. For this situation, quick connect-disconnect optical couples 52, 53 are provided.

Each socket 35, 36 is provided at the open base end with three radially extending thin, flexible tabs 39 preferably of uniform size and of uniform length T. A double-sided pressure sensitive tape 41 is secured to the bottom of each respective tab 39 and is used as a means of securing the respective socket 35 or 36 to the body surface. Removable covering strips may be employed to protect the adhesive material prior to installation. Additionally, as later referred to in connection with FIGS. 15 and 16 it will be noted that the critical distance X between the light source module 50 and light detector module 60 can be established by overlapping a pair of tabs 39 and using the length T as a locating device as best illustrated in FIG. 15. Pad 30 is formed with two slits 31, 32 leading from socket holes 33, 34 and spaced apart by the same critical distance X. Thus, the space between the slits 31, 32 can also be used as a spacing reference. Slits 31, 32 also facilitate assembly of pad 30 on the respective sockets 35, 36 after the respective optical modules 50, 60 have been fully nested in their respective sockets 35, 36 by allowing the respective outgoing optical cables 51, 61 secured through the respective quick disconnect couplings 52, 53 to pass through slits 31, 32 and over pad 30 during assembly of pad 30 on sockets 35, 36.

While serving different functions, optical modules 50 and 60 are basically of similar size and construction and will be more fully described in reference to FIGS. 2–7. Module 50, by way of example, comprises a hollow, circular-shaped housing 70 having a back coverplate 71 and a flat front face 72 formed with a central aperture 73. The fiber bundle 51 couples through quick disconnect optical coupling 52 and terminates with a right angle shaped terminal end 79 having a slightly protruding portion with a ground optical face 80 located in the aperture 73. The void within housing 70 surrounding the right angle shaped terminal end 79 is filled with an epoxy or similar hard-setting compound to facilitate securement of the terminal end 79 within housing 70 and back cover plate 71 is suitably glued or otherwise secured in place after such assembly.

Terminal end 79 of fiber bundle 51 provides both a near-infrared light source terminal and a corrective detector terminal with selected fibers being employed for bringing light to the point of light entry and other randomly dispersed selected fibers being employed for collecting light reflected back directly from or near (1-3 mms) the point of light entry. Since the manner in which such corrective and measured light sources operate is fully explained in the related prior patents previously referred to, such description will not be repeated here to avoid repetition.

Module 60, as previously stated, employs a similar construction to that of module 50 and mounts fiber bundle 61 connected through quick disconnect optical coupling 53 and having a right angle shaped terminal end 82 with a slightly protruding portion having a ground optical face 83. Bundle 61 is used as a means for collecting the measured reflected light for processing as fully explained in the related prior patents. Further, during the light measuring operation, modules 50 and 60 are mounted in their respective module sockets 35, 36 and are positioned on the body so as to maintain uniform the spacing X within the limits discussed in the related prior patents.

Shielding of ambient light is deemed critically important especially when metabolic trends are being monitored and discrete changes are significant though small in value. Thus, when the respective modules 50, 60 have been assembled in the respective sockets 35, 36 and are mounted as depicted in FIG. 1 with pad 30 adhesively secured over the respective socket tabs 39, an additional protective shielding is provided by employing the auxiliary pad of light shielding material 40 which is provided with double-sided adhesive tape 44 such that pad 40 can be firmly secured and provide adequate light shielding over the respective modules 50, 60 assembled in their respective sockets 35, 36 as depicted in FIG. 1. The corresponding optical cables 51, 61 are led out under pad 40 and are preferably wrapped with a black felt strip 48 at the point where the cables exit from beneath pad 40 to provide additional shielding. A dense, black, highly flexible, hard neoprene rubber sheet of 1/64" thickness has been found suitable for use in making pad 40.

As another aspect of the present invention, a pair of thin, double-sided, annular-shaped, pressure sensitive adhesive tapes 100, 101 are employed on the respective modules 50, 60 and are used to assist in providing the desired ambient light shielding around the respective optical faces 80, 83. Tapes 100, 101 are preformed in the shape illustrated in FIG. 17 and typically have removable adhesive protecting covering which, after removal, allows the respective tapes 100, 101 to be attached on one side to the respective modules 50, 60 while leaving the opposite adhesive surfaced side of the respective tapes 100, 101 exposed for securing to the respective body surfaces opposite the respective optical faces 80, 83.

In using the invention assembly 20 an optical gel is applied to each optical face 80, 83 and the respective annular adhesive tapes 100, 101 are installed around the respective optical faces 80, 83. The respective modules 50, 60 are then snugly fitted into their respective sockets 35, 36. In order to obtain the desired spacing X between the light source module 50 and the light detector module 60 the socket tabs 39 may be oriented prior to being adhered to the body surface as in FIG. 15 such that the socket tab length T maintains the correct distance X. In this mode of installation after the optical modules 50, 60 have been snugly fitted into their respective sockets 35, 36 as illustrated in FIGS. 11–12 for module 60 as an example, the respective covers for adhesive strips 41 may be removed from the socket tabs 39 and from annular tapes 100, 101 and the modules 50, 60 adhered to the body in the orientation illustrated in FIG. 15. After this step, the adhesive cover for the adhesive on pad 30 is removed and pad 30 is next installed over the assembled optical modules 50, 60 and sockets 35, 36 utilizing the slits 31, 32 to position the optical cables 51, 61 extending out over pad 30 as seen in FIGS. 1 and 16.

In another installation mode after the respective optical modules 50, 60 are snugly fitted into the respective sockets 35, 36 the sockets are installed in pad 30 as illustrated in FIG. 16 which utilizes the spacing between the slits 31, 32 to establish the desired spacing X required during the measuring operation. In this mode of installation, the covers for the adhesive on adhesive tapes 41 on socket tabs 39, the covers on the adhesive on annular tapes 100, 101 and the cover for the adhesive on pad 30 may well be removed after the respective sockets 35, 36 with the respective modules 50, 60 have been assembled in the manner of FIG. 16. The entire pad-socket-module assembly illustrated in FIG. 16 can then be adhered to the body utilizing the adhesive surfaces of the optical tapes 100, 101, the adhesive surfaces on the socket tabs 39 and the adhesive surface provided on the pad 30. The auxiliary pad 40 is then next installed in the manner previously described following which a suitable light shielding cape 45 is draped over the head and over those portions of the optical cabling proximate the assembly 20 to provide additional ambient light shielding.

From the foregoing description, various advantages over the light source-detector mounting arrangements set forth in the prior patents and the copending application Ser. No. 289,413 will become evident. A major advantage resides in the ability to secure the assembly 20 to the body, particularly to the head for brain monitoring, without requiring the use of a strap as previously described in the prior related patents and the referred to copending application. Thus, if it becomes necessary to tilt the head backward during the surgical or medical procedure, this can be accomplished without dislodging the monitoring assembly 20. Alternatively, when the head is not required to be tilted, the described invention apparatus lends itself to this application mode.

The respective sockets 35, 36 may be made of a suitable plastic and thus may be formed as relatively inexpensive single end-use components. Additionally, pad 30 may also be a disposable single end-use component as well as the auxiliary pad 40. Thus, by being able to provide these operating components in a form adapted to disposable, single end-use, substantial expense is saved with regard to washing and sterilizing the invention apparatus following a surgical or medical procedure.

The invention apparatus also achieves a significant advance in light shielding in being able to utilize the combined shielding characteristics of the annular tapes 100, 101 which surround the respective optical faces 80, 83 on modules 50, 60 in conjunction with the shielding properties of pad 30 which can be tightly secured by means of the adhesive 38 on the surface of pad 30. Additional shielding is, of course, provided by the auxiliary shielding pad 40 utilizing the adhesive strips 44.

What is claimed is:

1. Spectrophotometric measuring apparatus for measuring a selected activity of a selected portion of a human body where such activity bears a measurable relation to an absorption characteristic of the selected portion for a particular wavelength of light, including in combination:
    (a) first optical cable means providing a bundle of optical fibers with selected fibers connected for receiving and transmitting the output light emissions of light sources at measuring and reference wavelengths to a selected point of light entry on said selected portion of said body and other selected fibers connected for receiving and transmitting light emissions reflected directly back from said selected point of light entry to a processing means;
    (b) second optical cable means providing a bundle of optical fibers connected for receiving and transmitting light emissions reflected and scattered to a selected point of light exit on said selected portion of said body to a processing means;
    (c) a first preformed optical module comprising a molded cylindrical hollow housing enclosing first light guide means formed by a right-angle-shaped bundle of optical fibers optically coupled at one end to said first optical cable means and at the opposite end having a first optical light emitting face centrally positioned in an outer face of said housing and adapted to be mated in a substantially pressed fit relation with said selected point of light entry;
    (d) a second preformed optical module comprising a second molded cylindrical hollow housing of the same size as said first housing and enclosing second light guide means formed by a right-angle-shaped bundle of optical fibers optically coupled at one end to said second optical cable means and at the opposite end having a second optical light receiving face centrally positioned in an outer face of said second module housing and adapted to be mated in a substantially pressed-fit relation with said selected point of light exit;
    (e) first and second socket structures of similar size, each being molded as an integral internally-hollow structure having a cylindrical side wall with an open base end and an opposite closed end, a slot in the wall structure for passing therethrough a respective optical fiber bundle leading from a respective said module, and a plurality of thin flexible tab members of uniform size and length extending radially outward from and circumferentially spaced on said base end, said first socket structure being adapted to receive in snug-fit relation said first optical module housing with the optical cable connected end portion of the fiber bundle associated with said first optical module passing through the slot of said first socket side wall and the said second socket structure being adapted to receive in snug-fit relation said second optical module with the optical cable connected portion of the fiber bundle associated with said second optical module passing through the slot of the said second socket side wall, and including adhesive means on the bottom surfaces of said tab members enabling the tab members of said first socket structure to be secured to the body in laterally spaced relation with respect to the tab members of the second socket structure whereby to secure said optical modules in correspondingly-spaced relation; and
    (f) a flexible light-shielding pad having one adhesive surfaced side, having a pair of apertures formed to receive said socket structures in a predetermined spaced relation, having slit portions of said pad connecting said apertures to an outer edge thereof thereby enabling said shielding pad to be fitted over said tab members while allowing the optical cables associated with said modules to lead away from said shielding pad over and above the outer surface thereof and in a manner enabling said adhesive surfaced side to be adhesively secured to the body and the respective optical faces of said modules to be light shielded by said adhesively faced side of said panel.

2. A spectrophotometric measuring apparatus as claimed in claim 1 wherein said plurality of tab members comprise three said tab members circumferentially equally spaced on said base end and the length of said tab members corresponds to a length of measure by which said predetermined spaced relation may be established.

* * * * *